US005258005A

United States Patent [19]

Christian

[11] Patent Number: 5,258,005

[45] Date of Patent: Nov. 2, 1993

[54] ATRAUMATIC GRASPING DEVICE FOR LAPAROSCOPIC SURGERY

[75] Inventor: Jeffrey J. Christian, San Jose, Calif.

[73] Assignee: Unisurge, Inc., Cupertino, Calif.

[21] Appl. No.: 807,075

[22] Filed: Dec. 13, 1991

[51] Int. Cl.[5] .............................................. A61B 17/28

[52] U.S. Cl. ..................................... 606/205; 606/210

[58] Field of Search ............... 606/205, 206, 207, 209, 606/106, 107, 208, 210; 128/751; 294/100

[56] References Cited

U.S. PATENT DOCUMENTS

| | | | |
|---|---|---|---|
| 2,212,013 | 9/1939 | Devareux | 294/100 |
| 2,585,098 | 2/1952 | Elliott | 294/100 |
| 4,085,743 | 4/1978 | Yoon | 606/206 |
| 5,094,247 | 3/1992 | Hernandez et al. | 128/751 |

FOREIGN PATENT DOCUMENTS

| | | | |
|---|---|---|---|
| 1171354 | 5/1964 | Fed. Rep. of Germany | 294/100 |
| 1563730 | 4/1970 | Fed. Rep. of Germany | 294/100 |

*Primary Examiner*—Edgar S. Burr
*Assistant Examiner*—Anthony H. Nguyen
*Attorney, Agent, or Firm*—Flehr, Hohbach, Test, Albritton & Herbert

[57] ABSTRACT

Atraumatic grasping device for use in surgery, having an elongate tubular member having proximal and distal extremities. An insert is carried by the distal extremity of the tubular member and forms a slot opening into the tubular member. First and second elongate substantially parallel spring members having proximal and distal extremities. The first and second spring members extend through the tubular member and through the slot so that the distal extremities of the first and second spring members extend beyond said slot. The distal extremities of the first and second spring members are bowed apart from each other. First and second jaws formed on the distal extremities of the first and second spring members. A linkage is secured to the proximal extremities of the first and second spring members and the tubular member for causing relative movement between the tubular member and the first and second spring members to cause closing and opening of said first and second jaws in a substantially parallel motion to facilitate grasping of tissue and retaining the same between the first and second jaws.

5 Claims, 2 Drawing Sheets

44 47 46 48 49 11 41 36 41 32 13 42 31 34 37 33 12 16 17 22 14 4 19 14 21 16a 19 17a 26 28 27

ATRAUMATIC GRASPING DEVICE FOR LAPAROSCOPIC SURGERY

This invention relates to an atraumatic grasping device for laparoscopic surgery.

Jaw-type devices have heretofore been provided for laparoscopic surgery. Typically such jaw-type devices have serrated jaws which are pivotally mounted having a gripping action which makes it difficult to grasp and hold onto certain types of tissue as for example a bloated gall bladder. When grasping tissue of such a character with such jaw-type devices there is a tendency to push the tissue out of the jaws as the jaws are closing. There is, therefore, a need for an improved grasping device which will overcome such difficulties.

In general, it is the object of the present invention to provide an atraumatic grasping device for use in laparoscopic surgery which utilizes a parallel closing action to provide improved gripping capabilities.

Another object of the invention is to provide a device of the above character in which the jaws are provided with high-grip surfaces.

Another object of the invention is to provide a device of the above character in which a grasping action takes place in which the distal extremities of the jaws remain in a fixed longitudinal position as the jaws are closed.

Another object of the invention is to provide a device of the character which can be readily operated by one hand.

Another object of the invention is to provide a device of the above character in which the jaws can be locked in a predetermined grasping position.

Additional objects and features of the invention will appear from the following description in which the preferred embodiments are set forth in detail in conjunction with the accompanying drawings.

Figure 1:
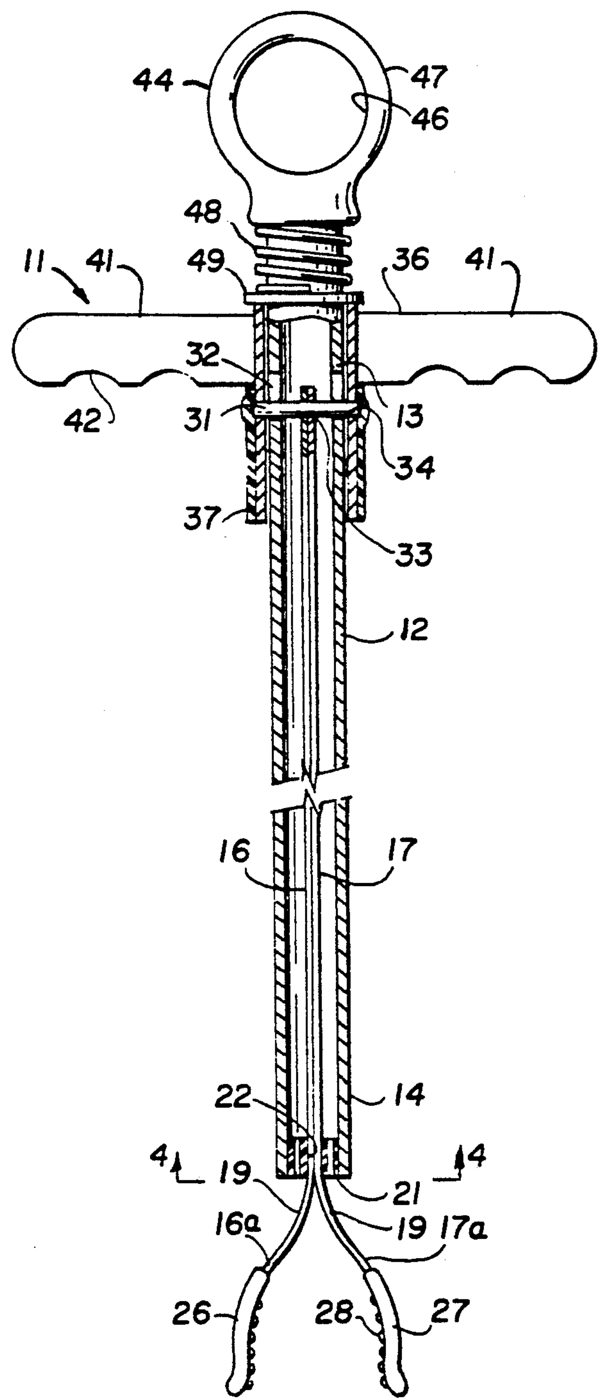
FIG. 1 is a side-elevational view partially in cross-section of an atraumatic grasping device for laparoscopic surgery incorporating the present invention and showing the jaws in an open position.
Figure 2:
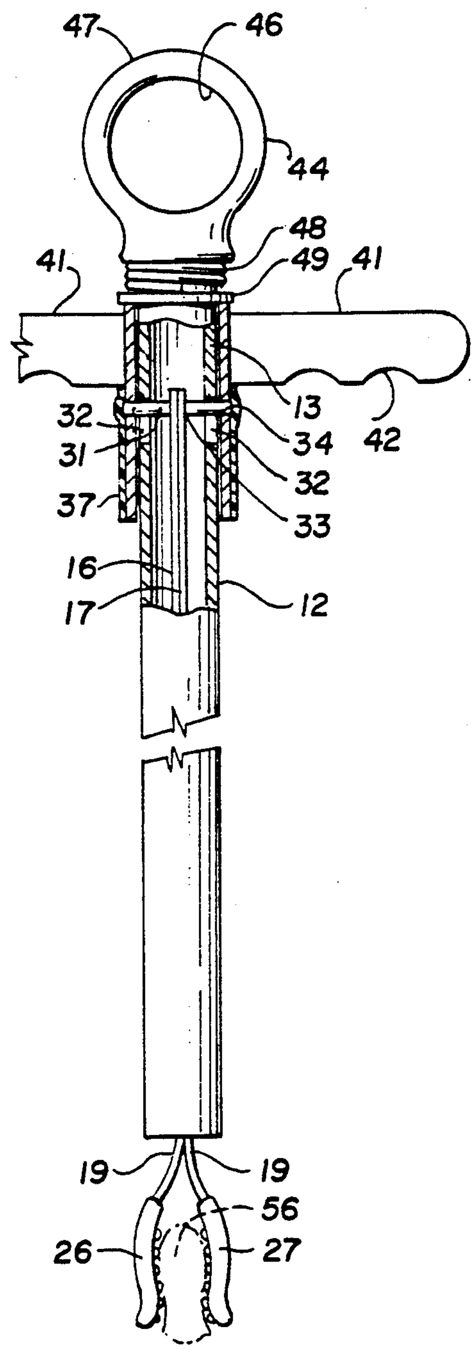
FIG. 2 is a side-elevational view similar to FIG. 1 partially in cross-section, but showing the jaws in a closed position.
Figure 3:
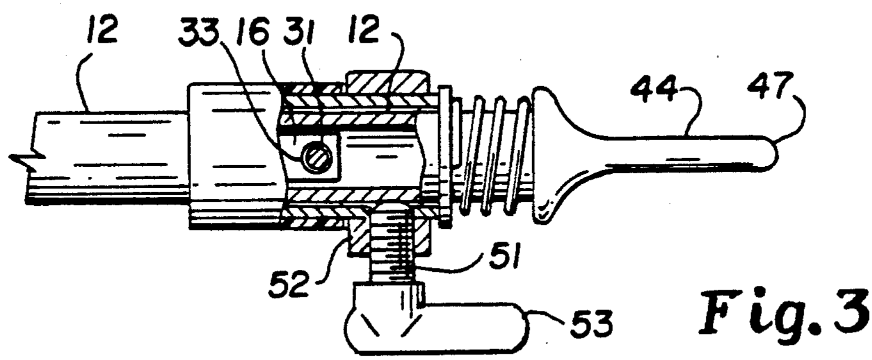
FIG. 3 is a partial view partially in cross-section of the proximal of the device shown in FIG. 1.
Figure 4:
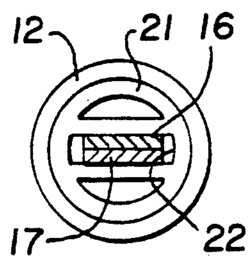
FIG. 4 is a cross-sectional view taken along the line 4—4 of FIG. 1.

In general, the atraumatic grasping device for laparoscopic surgery consists of an elongate tubular member having proximal and distal extremities. Means is secured to the distal extremity of the tubular member forming a slot opening into the tubular member. First and second elongate substantially parallel members having proximal distal extremities are provided. The first and second members extend through said tubular member and through said slot so that the distal extremities of the first and second members extend beyond said slot. The distal extremities of said first and second members are bowed outwardly with respect to each other. First and second jaws are formed on the distal extremities of said first and second members. Means is secured to the proximal extremities of said first and second members and to said tubular member for causing relative movement between said tubular member and said first and second members to cause closing and opening of said first and second jaws with respect to each other to facilitate the grasping of tissue and retaining that tissue between the first and second jaws.

More particularly, as shown in FIGS. 1–4 of the drawings, the atraumatic grasping device 11 consists of an elongate tubular member 12 having proximal and distal extremities 13 and 14. The tubular member 12 can be formed of a suitable material such as plastic or metal. First and second elongate flat substantially parallel spring members 16 and 17 are provided which are formed of a suitable material such as spring steel. The members 16 an 17 have proximal and distal extremities 18 and 19.

An insert 21 is provided within the distal extremity of tubular member 12 and is provided with a rectangular slot 22 which extends diametrically of the tubular member 12 and lies in a plane which is parallel to the longitudinal axis of tubular member 12. The insert 21 is secured in distal extremity 14 of the tubular member 12 by suitable means such as adhesive (not shown).

The first and second flat spring members 16 and 17 are disposed parallel to each other with the wide sides of the same facing each other and extend longitudinally of the tubular member within the tubular member 12 and through the rectangular slot 22. As can be seen from FIG. 4, the slot 22 is sized so that the spring members 16 and 17 can slidably fit therein while maintaining the parallel orientation of the spring members 16 and 17. The distal extremities of the spring members 16 and 17 extend beyond the distal extremity 14 of the tubular member 12. The distal extremities 19 of the spring members 16 and 17 are bowed outwardly with the flat surfaces facing each other having bowed portions 16a and 17a therein with the bows being in the longitudinal axes of the spring members 16 and 17.

First and second jaws 26 and 27 are formed on the distal extremities 19 of the spring members 16 and 17 and in the bowed portions 16a and 17a as shown in FIG. 1. The jaws 26 and 27 are formed of an elastomeric thermoplastic material such as silicone or urethane-based compounds. A specific materials utilizable for this purpose is Krayton TM. This material should be one which provides a high gripping force and has a tacky or sticky surface. In other words, the material should have a high coefficient of friction to facilitate the grabbing of tissue.

Figure 5A:
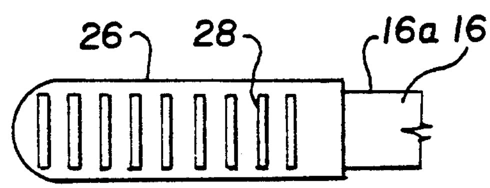
FIGS. 5A, 5B and 5C show different types of raised surfaces which can be provided on the inner surfaces of the jaws of the device shown in FIGS. 1–4.
Figure 5B:
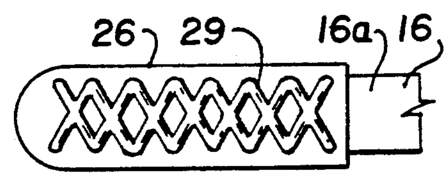
Figure 5C:
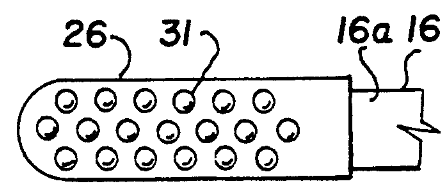

In order to impart additional gripping capabilities to the jaws 26 and 27 they are provided with raised portions which face inwardly towards each other. As can be seen, particularly from FIG. 5A, serrations 28 can extend transversely of the longitudinal axis of the spring member 16. Alternatively, the raised portions can be provided by a plurality of raised crosses 29 as shown in FIG. 5B or by raised spaced apart hemispherical protrusions 31 as shown in FIG. 5C.

Means is secured to the proximal extremities of the spring members 16 and 17 and to the proximal extremity of the tubular member 12 to cause relative movement between the spring members 16 and 17 and the tubular member 12 to cause closing and opening of the distal extremities 19 and the portions 16a and 17a to facilitate the grasping of tissue and retaining the tissue between the jaws. Such means consists of a pin 31 extending diametrically of the tubular member 12 and extending through elongate slots 32 provided on opposite side walls of the tubular member 12 (see FIG. 1) and extending through holes 33 provided in the proximal extremities of spring members 16 and 17. The pin 31 also extends through holes 34 provided in a cylindrical sleeve 36 slidably mounted and concentrically disposed on the proximal extremity 13 of the tubular member 12. The pin 31 is retained in place by a length of shrink-fit tubing 37 which overlies the ends of the pin 31 and serves to retain the pin 31 in place.

A handle 41 is mounted on the sleeve so it is clear of the pin 31 and is secured thereto by suitable means such as welding. The handle 41 extends diametrically of both sides of the sleeve 36 and is provided with arcuate recesses 42 which are adapted to be engaged by the fingers of a hand. The handle 44 is provided on the proximal extremity of the tubular member 12 and is secured thereto by suitable means such as welding. The handle 44 has a circular configuration with a central opening 46 therein which is adapted to be engaged by the finger of a hand. The handle 44 is also provided with a curved outer surface 47 which is adapted to be engaged by the palm of the hand with the fingers grasping the handle 41.

Means is provided for yieldably returning the tubular member 12 and the spring members 16 and 17 into positions relative to each other so that the jaws 26 and 27 are normally in an open position and consists of a spring 48 which is mounted on the tubular member 12 below the handle 44 and engaging a washer 49 overlying the sleeve 36. The length of the slots 32 determines the amount of travel of the tubular membrane 12 with respect to the spring members 16 and 17 and thereby determine the length of travel between open and closed positions.

Means is provided for locking the sleeve 36 in the desired longitudinal position with respect to the tubular member 12 and consists of a thumbscrew 51 threaded into a boss 52 mounted on the sleeve 36. This permits the thumbscrew 31 to frictionally engage the tubular member 12 by use of the handle 53 mounted on the screw 51. The handle 53 is adapted to be engaged by a finger of the hand as, for example, the thumb.

Operation and use the atraumatic grasping device in a laparoscopic surgical procedure may now be briefly described as follows. Let it be assumed that a laparoscopic surgery is underway and that it is desired to utilize the atraumatic grasping device 11 for manipulating tissue, as, for example, a diseased gall bladder. The device 11 can be introduced into the abdominal cavity of the patient through an introducer assembly of the type described in co-pending application Ser. No. 07/807,101, filed Dec. 13, 1991, now U.S. Pat. No. 5,176,648. In order to pass through the introducer, the device 11 can be operated to move the jaws 26 and 27 towards a closed position by having one hand of the surgeon engaging the device by having the hand engage the curved surface 47 of the ring handle 44 and then having two fingers engage the handle 41 on opposite sides of the sleeve 36. As soon as the distal extremity of the grasping device 11 has been passed through the introducer assembly, the jaws can be moved into a position adjacent to the gallbladder to be manipulated. The jaws can be permitted to open under the yieldable force provided by the spring 46 permitting the tubular member 12 to slide toward the proximal extremities of the spring members 16 and 17. As this occurs, the jaws 26 and 27 will move to the open position as shown in FIG. 1.

The device can then be advanced so that the jaws 26 and 27 extend over the tissue, as, for example, a gall bladder 56. The gall bladder can then be grasped by holding the handle 41 stationary and moving the handle 44 inwardly to thereby cause the tubular member 12 to move towards the distal extremities of the spring members 16 and 17 to cause closing of the jaws 26 and 27 around the gall bladder 56 with the jaws 26 and 27 remaining in the same longitudinal position with respect to the gall bladder being removed. As soon as the gall bladder 56 has been firmly grasped, the gall bladder can be excised in the conventional manner and then removed by pulling outwardly on the atraumatic grasping device 11 without causing damage or injury to the tissue being removed. The grasping action utilized for such tissue removal is particularly efficacious because the jaws 26 are moved toward the closed position in a generally parallel relationship permitting the very tip or distal extremity of the jaws to first engage the tissue and to clamp the tissue between the jaws 26 and 27. The grasping action hereinbefore described is also efficacious because since the tubular member 12 moves relative to the spring member 16 and 17, the distal extremities of the jaws 26 and 27 remain in the most forward position and do not move rearwardly or proximally as the jaws are moved to a closed position. This is particularly advantageous for removing tissue which has become bloated, swollen or diseased. By providing the jaws 26 and 27 of a material which has a high gripping force, it is possible to grip the tissue firmly yet atraumatically without permitting the tissue to slip out from between the jaws 26 and 27.

After the tissue has been firmly grasped within the jaws 26 and 27, the atraumatic grasping device 11 can be removed through the introducer carrying with it the tissue desired to be removed. As soon as the device is outside of the introducer, the physician can release the handle 41 or 44 permitting the tube 12 under the force of the spring 48 to slide in a direction towards the distal extremity of the spring members 16 and 17 permitting the jaws 26 and 27 to open and release the tissue 56 therefrom.

If desired, the jaws 26 and 27 can be retained in the desired position by operating the screw handle 53 as, for example, by the thumb of the hand to tighten the same to frictionally engage the tubular member 12 and to thereby prevent relative movement between the tube 12 and the spring members 16 and 17.

It is apparent from the foregoing that there has been provided an atraumatic grasping device which is particularly useful in laparoscopic surgery for grasping, manipulating and removing tissue from within the body of the patient. The parallel action movement of the jaws provides an improved gripping capability for the device. In addition, the jaws with raised portions being formed out of a material having high gripping capabilities also facilitate grasping tissue within the body.

I claim:

1. In an atraumatic grasping device for use in surgery, an elongate tubular member having proximal and distal extremities, an insert carried by the distal extremity of the elongate tubular member forming a rectangular slot opening into the tubular member and extending diametrically of the tubular member, first and second elongate substantially parallel spring members having proximal and distal extremities, said first and second spring members extending through said elongate tubular member and through said slot so that the distal extremities of the first and second spring members extend beyond said slot, said distal extremities of said first and second spring members being bowed apart from each other, first and second jaws formed on the distal extremities of the first and second spring members and means secured to the proximal extremities of said first and second spring members and to said tubular member for causing relative movement between said tubular member and said first and second spring members to cause closing and opening of said first and second jaws in a substantially parallel motion to facilitate grasping of tissue and retaining the same between the first and second jaws.

2. A device as in claim 1 wherein said jaws are formed of a material having a high gripping capability.

3. A device in claim 1 wherein said first and second spring members are formed so that closing of the jaws occurs with the distal extremities of the jaws remaining in the same longitudinal position with respect to the tissue as the tubular member is moved distally towards the distal extremities of the jaws during the time that the jaws are being moved to a closed position.

4. A device as in claim 1 wherein said spring members are in the form of flat generally parallel metal members.

5. A device as in claim 1 wherein said means secured to the proximal extremities of said first and second spring members and to said elongate tubular member includes a sleeve slidably mounted on said tubular member, said tubular member having a pair of slots extending longitudinally thereof, a pin secured to said sleeve and extending through said slots and handle means carried by said sleeve and by the proximal extremity of said tubular member.

* * * * *